(12) United States Patent
Vidalinc

(10) Patent No.: US 7,682,505 B2
(45) Date of Patent: Mar. 23, 2010

(54) METHOD AND DEVICES FOR DRY LOADING OF CHROMATOGRAPHY RESINS

(75) Inventor: Pierre Vidalinc, Chaptuzat (FR)

(73) Assignee: Bio-Rad Pasteur, Marnes-la-Coquette (FR)

( * ) Notice: Subject to any disclaimer, the term of this patent is extended or adjusted under 35 U.S.C. 154(b) by 396 days.

(21) Appl. No.: 10/590,362

(22) PCT Filed: Feb. 14, 2005

(86) PCT No.: PCT/EP2005/002364

§ 371 (c)(1),
(2), (4) Date: Aug. 23, 2006

(87) PCT Pub. No.: WO2005/080962

PCT Pub. Date: Sep. 1, 2005

(65) Prior Publication Data

US 2007/0193933 A1    Aug. 23, 2007

Related U.S. Application Data

(60) Provisional application No. 60/546,170, filed on Feb. 23, 2004.

(30) Foreign Application Priority Data

Feb. 23, 2004    (EP)    ................................. 04290481

(51) Int. Cl.
*B01D 15/08*    (2006.01)

(52) U.S. Cl. .................................. 210/198.2; 210/656

(58) Field of Classification Search .............. 210/198.2, 210/635, 656, 657, 659; 96/101, 105, 106; 141/12, 80
See application file for complete search history.

(56) References Cited

U.S. PATENT DOCUMENTS

| | | | | |
|---|---|---|---|---|
| 1,738,213 | A | * | 12/1929 | Snow ........................ 210/535 |
| 2,804,102 | A | * | 8/1957 | Cooksley et al. .............. 141/20 |
| 2,974,691 | A | * | 3/1961 | Bingham .................... 141/142 |
| 3,339,811 | A | * | 9/1967 | Haag .......................... 222/394 |
| 3,385,327 | A | * | 5/1968 | Granier ....................... 141/39 |

(Continued)

FOREIGN PATENT DOCUMENTS

DE    39 01 773    7/1990

(Continued)

OTHER PUBLICATIONS

Hofmann M: "A novel technology for packing and unpacking pilot and production scale columns" Journal of Chromatography A, vol. 796, No. 1, Feb. 13, 1998, pp. 75-80, XP004108671.

(Continued)

*Primary Examiner*—Ernest G Therkorn
(74) *Attorney, Agent, or Firm*—Nixon & Vanderhye P.C.

(57) ABSTRACT

A module (1) for dry loading and unloading of a chromatography resin, a chromatography column (3) and a method for using such a module (1). The column (3) comprises an inlet valve (39) adapted to load dry chromatography resin particles and an outlet port (35) for pumping the air from de column (3). The outlet port (35) is located above the inlet valve (39).

6 Claims, 2 Drawing Sheets

U.S. PATENT DOCUMENTS

| | | | | |
|---|---|---|---|---|
| 3,583,230 | A | * | 6/1971 | Patterson .................. 73/864.85 |
| 4,437,487 | A | * | 3/1984 | Marmon ..................... 137/322 |
| 4,719,011 | A | * | 1/1988 | Shalon et al. ............ 210/198.2 |
| 5,169,522 | A | * | 12/1992 | Shalon et al. ............ 210/198.2 |
| 5,244,017 | A | * | 9/1993 | Hartman et al. ................. 141/5 |
| 5,282,973 | A | | 2/1994 | Mann |
| 5,329,975 | A | * | 7/1994 | Heitel ......................... 141/19 |
| 5,667,676 | A | * | 9/1997 | Alaska .................... 210/198.2 |
| 5,788,127 | A | * | 8/1998 | Hanmer ...................... 222/422 |
| 6,190,560 | B1 | * | 2/2001 | Mann ......................... 210/656 |
| 6,997,439 | B2 | * | 2/2006 | Miyazaki et al. ............ 251/324 |
| 7,208,085 | B2 | * | 4/2007 | Geng et al. ............... 210/198.2 |

FOREIGN PATENT DOCUMENTS

| | | |
|---|---|---|
| DE | 39 01 773 A1 | 7/1990 |
| EP | 0 150 780 | 8/1985 |
| EP | 0 150 780 A | 8/1985 |
| EP | 0 279 257 | 8/1988 |
| EP | 0 279 257 A | 8/1988 |
| EP | 1348957 * | 2/2002 |
| EP | 1 348 957 | 10/2003 |
| EP | 1 348 957 A | 10/2003 |
| JP | 8 94603 | 4/1996 |
| JP | 08 094603 A | 4/1996 |

OTHER PUBLICATIONS

International Search Report of PCT/EP2005/002364, mailed Sep. 20, 2005.

Patent Abstracts of Japan, JP 08 094603, Apr. 12, 1996, vol. 1996, No. 8, Aug. 30, 1996.

Hoffmann, Journal of Chromatography A, vol. 796, No. 1, Feb. 13, 1998, pp. 75-80.

Patent Abstracts of Japan, JP 2004 004093, Jan. 8, 2004, vol. 2003, No. 12, Dec. 5, 2003.

European Search Report issued in connection with EP 04 29 0481.

International Search Report issued in connection with PCT/EP2005/002364.

* cited by examiner

METHOD AND DEVICES FOR DRY LOADING OF CHROMATOGRAPHY RESINS

This application is a 371 and the US national phase of International application PCT/EP2005/002364, filed 14 Feb. 2005, which designated the U.S. and claims priority of EP 04290481.3, filed 23 Feb. 2004, and U.S. 60/546,170, filed 23 Feb. 2004, the entire contents of each of which are hereby incorporated by reference.

The present invention relates to a chromatography column, a module comprising such a chromatography column and a method for using such a column or module.

The use of chromatography columns for the separation of individual compounds that exist in sample solution are well-known. Such columns are usually used for liquid chromatography. To this end, a resin is packed in an enclosure and a carrier liquid flows through the packed resin.

To load the resin in a column, one can open the column and pour in it the resin in suspension in a diluted buffer. One can also load the resin in a column via an automatic transfer pumping unit. At present, resins are loaded in columns in liquid phase. For this reason, the resins are usually stored and marketed in a buffer solution in order to avoid bacterial proliferation. After the loading, before the packing procedure, the storage buffer has to be replaced, by an appropriate buffer (phosphate buffer, chloride buffer, etc.).

Alternatively, the present invention provides a method for loading a chromatography resin into a chromatography column comprising an enclosure, a first port, to put the enclosure in communication with a tank comprising chromatography resin particles having a size distributed between a minimum size and a maximum size, and a second port, to put the enclosure in communication with a pump, wherein the first port forms a passage having a minimum section which is at least 10 000 times as large as a particle section corresponding to the maximum size particles.

Such a method allows the use of a dry resin. A dry resin can be carried in sealed bags. Such bags can be sterilized, for instance with gamma rays.

Thus, resins can be conditioned without antibacterial buffer. Consequently, the resin conditioning is easier than with the prior art methods.

With the loading method according to the invention, there is no need to condition the resin in a liquid phase. Thus, the storage volume and weight are lesser than with the prior art methods. The transport and storage costs are also reduced.

Further, the resin volume transferred in a column can be accurately controlled since the only resin can be weighted.

Handling the resin is also easy since the overweight due to the storage buffer is suppressed. Moreover, it is not necessary to put the resin in suspension in the buffer before its transfer in a column.

Buffer volumes required for the packing and the unpacking of the columns are reduced. Once the dry resin has been transferred in a column, it can be dampened directly with the packing buffer, without flushing the storage buffer.

Consequently, further to the easy resin handling, conditioning and weighing, the loading method according to the invention allows to make the packing easier.

Embodiments of the invention may include one or more of the following features. The column comprises an enclosure having a first port and a second port, and said method comprises pumping a dry chromatography resin from a resin tank into the enclosure through the first port, via a pump connected to a second port. The enclosure, when in use, extends vertically between a bottom and a top, the second port being located above the first port. A pump is connected to the second port. It pumps the resin through a filter. The vacuum pressure in the enclosure is between −100 kPa and −50 kpa.

Another aspect of the invention provides a method for unloading a chromatography resin mixed with a liquid, from a chromatography column into a chromatography column comprising an enclosure, a first port, to put the enclosure in communication with a tank comprising chromatography resin particles having a size distributed between a minimum size and a maximum size, and a second port, to put the enclosure in communication with a pump, wherein the first port forms a passage having a minimum section which is at least 10 000 times as large as a particle section corresponding to the maximum size particles.

Embodiments of such an unloading method may include one or more of the following features. The column comprises an enclosure having a high port located above a low port, this method comprises successively the steps of a) pumping the liquid from the enclosure through the low port, b) drying the chromatography resin comprised in the enclosure, and c) pumping the dried resin through the low port. The vacuum pressure in the enclosure is between −100 kPa and −50 kPa. The unloading method according to the invention further comprises between steps b) and c), injecting a gas through the low port. Step b) of this method comprises injecting a hot gas through the low port in order to totally dry the resin. Step b) may also comprise injecting a hot gas through the high port. The hot gas can be steam, even if steam is not used in 100% of the unloading cases.

Another aspect of the invention provides a chromatography column comprising an enclosure and a first port. The first port puts the enclosure in communication with a tank comprising chromatography resin particles having a size distributed between a minimum size and a maximum size (these minimum and maximum can be for example respectively 10 µm and 300 µm, but most common sizes are comprised between 40 and 80 µm; of course the pore size of column filters is adapted to the particle size) This chromatography column also comprises a second port. The second port puts the enclosure in communication with a pump. Further, in this chromatography column, the first port forms a passage having a minimum section which is at least 10 000 times as large as a particle section corresponding to the maximum size particles. Of course the particle section corresponds to the maximum section of a particle.

Embodiments of this column may include one or more of the following features. The enclosure, when in use, extends vertically between a bottom and a top, the second port being located above the first port. The first port is provided with an inlet valve having a minimum section which is at least 10 000 times as large as the particle section corresponding to the maximum size particles.

Another aspect of the invention provides a chromatography column comprising an enclosure, a first port provided with an inlet valve, to put the enclosure in communication with a tank comprising chromatography resin particles having a size distributed between a minimum size and a maximum size, and a second port, to put the enclosure in communication with a pump, wherein the inlet valve comprises a chamber, an inlet duct and a piston, the chamber communicating with the enclosure through a first aperture, the inlet duct communicating with the chamber through a second aperture and being adapted to be connected to the tank, and the piston being movable in the chamber between a closing position, where it closes the first and second apertures, and an opening position, where it opens the first and second apertures, said piston letting free substantially all the space of the chamber between the first and second apertures.

BRIEF DESCRIPTION OF THE DRAWINGS

Embodiments of this column may include one or more of the following features. The enclosure, when in use, extends vertically between a bottom and a top, the second port being located above the first port.

The valve defines a passage between a pipe adapted to be connected to the duct and the enclosure, the smallest section of this passage through the valve corresponding to the section of one of the first and second apertures. The minimum section of the passage is at least 10 000 times as large as the particle section corresponding to the maximum size particles. The piston has an end surface with a tapered shape, said end surface having a portion which is flush with the internal surface of the enclosure, when in closing position. The first port forms a passage having a minimum section corresponding to at least a minimum internal diameter of 20 mm.

Another aspect of the invention provides a module for loading chromatography resin into a chromatography column. Such a module comprises a chromatography column according to the invention and the pump connected to the second port of the chromatography column, through a pipe.

In an embodiment of this module, it may include a tank for chromatography resin, this tank being connected to the first port.

Figure 1:
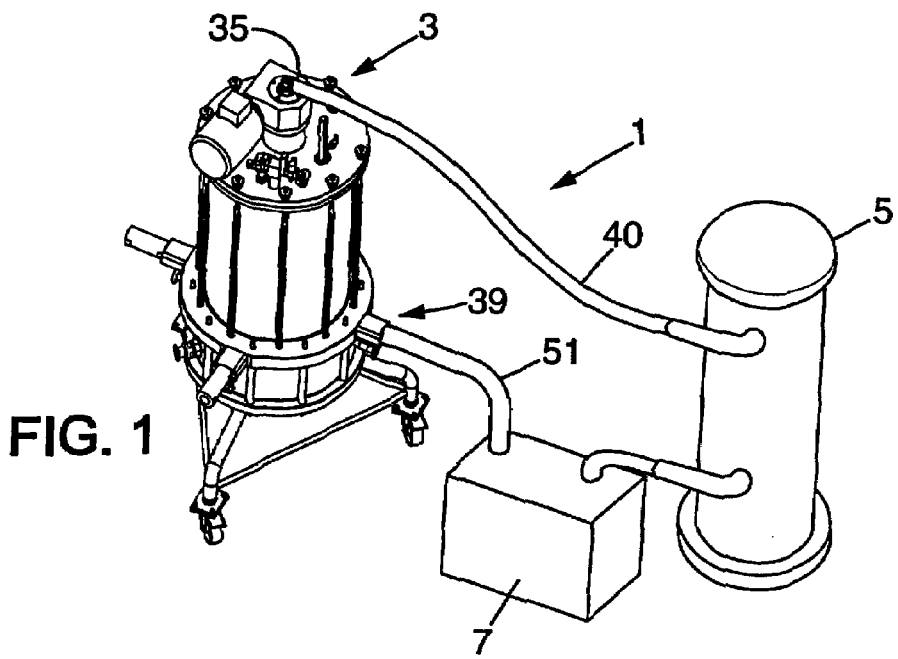

FIG. 1 shows an embodiment of a module of the present invention.

Figure 2:
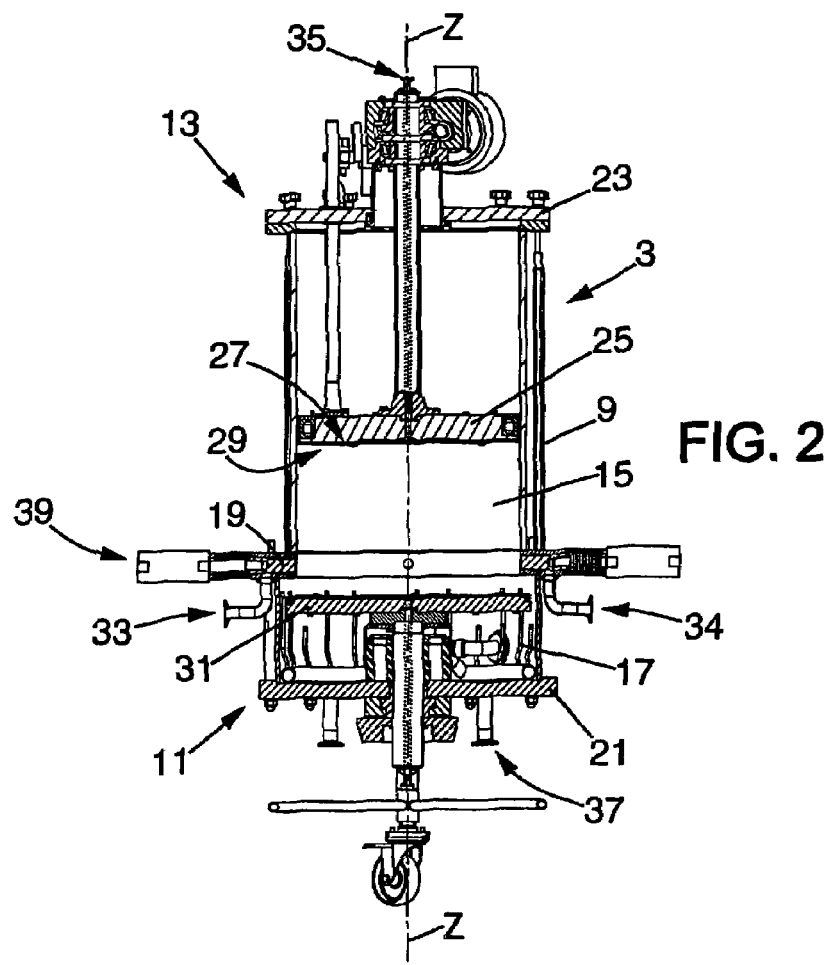

FIG. 2 is a vertical section of the chromatography column of the module shown in FIG. 1.

Figure 3A:
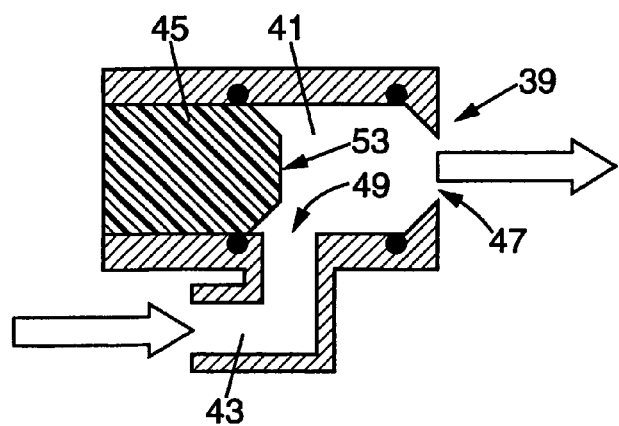
Figure 3B:
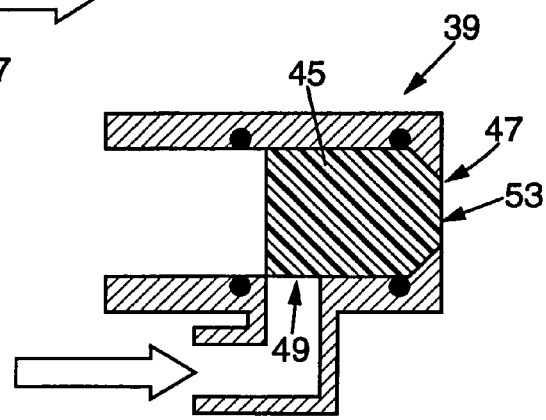

FIGS. 3a and 3b are schematic vertical sections of an example of a valve for the column shown on FIGS. 1 and 2, respectively in an opening position and a closing position.

Figure 4:
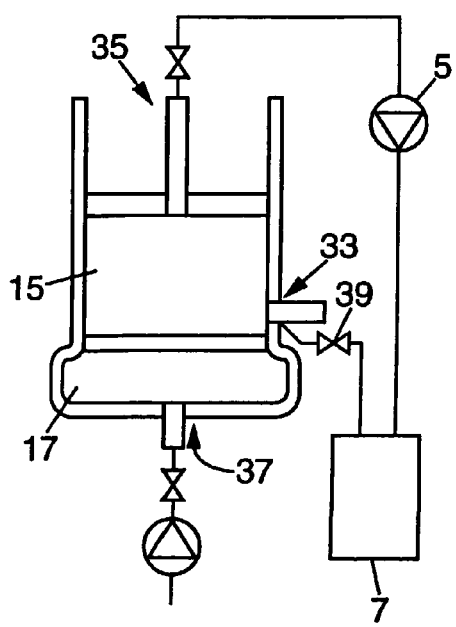

FIG. 4 is a schematic diagram of a module embodiment according to the invention.

Figure 5:
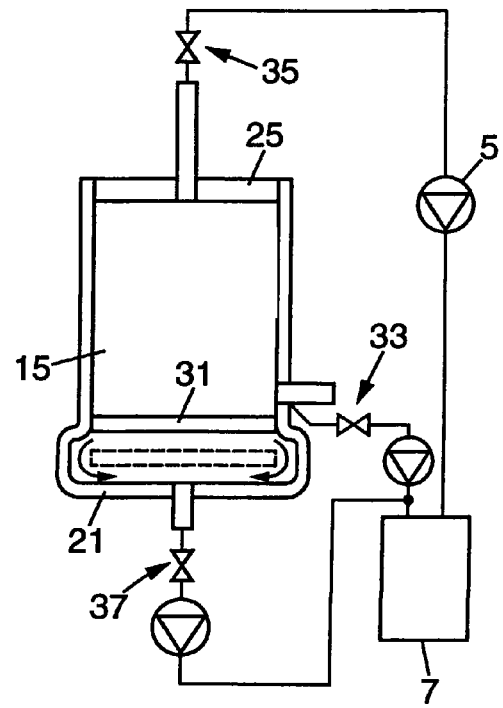

FIG. 5 is a schematic diagram of another module embodiment according to the invention.

DESCRIPTION OF THE PREFERRED EMBODIMENTS

FIG. 1 shows a first embodiment of the invention. According to this embodiment, the invention comprises a module 1 for loading a dry chromatography resin into a chromatography column. This module 1 comprises a chromatography column 3, a pump 5 and a resin tank 7.

The pump 5 is for instance a pump referenced C 21 04-200, marketed by PIAB USA, Inc. Such a pump can be controlled in order to have a vacuum in the chromatography column comprised about −75 kPa, with a flow rate of 2.5 m$^3$/mn. This pump is supplied with silicone sealings and filters in accordance with FDA requirements. The filters are for instance Gore™ Sinbran™ filters recommended for powders with particle size at least equal to 0.5 µm (depending on the powder properties). Gore™ Sinbran™ filters can be sterilized for 30 mn at 121° C.

As shown in FIG. 2, the chromatography column 3 comprises an enclosure 9 extending along a vertical axis Z between a bottom 11 and a top 13. The column 3 can be a column of the type marketed by Bio-Rad Laboratories Inc. by the EasyPack™ and GelTec™ trademarks (of Verdot Industrie).

The enclosure 9 consists of a first cylinder and a second cylinder, each having a longitudinal axis corresponding to the vertical axis Z. The first cylinder defines a separation chamber 15. The second cylinder defines a cleaning chamber 17. The second cylinder has a larger diameter than the first cylinder. The bottom edge of the separation chamber 15 is attached to the top edge of the cleaning chamber 17 by means of an annular plate 19. A bottom base plate 21 is attached to the bottom edge of the cleaning chamber 17. A top base plate 23 is attached to the top edge of the separation chamber 15.

A packing piston 25 moves in the separation chamber 15. The packing piston 25 comprises a distributor plate 27 and a frit 29 adapted to retain the resin in the separation chamber 15. For example, the frit 29 is pressed stainless steel or polypropylene with a 20 µm porosity. The combination of the distributor plate 27 and frit 29 ensures optimal uniform plug flow at all flow rates.

A bottom unpacking piston 31 is displaceable between an opened position, in which the separation chamber 15 opens into the cleaning chamber 17 to allow emptying the separation chamber 15 (as shown in FIG. 2), and a closed position in which the separation chamber 15 is isolated from the cleaning chamber 17 (not shown).

The enclosure 9 is provided with at least tree ports 33, 35, 37:
a first port 33 allows connection to the separation chamber 15 through the annular plate 19;
a second port, or high port, 35 allows connection to the separation chamber 15 through the packing piston 25; and
a low port 37 allows connection to the cleaning chamber 17 through the bottom base plate 21.

Another port 34 symmetrical to the first fort relatively to the vertical axis Z is possibly provided. This other port 34 allows connection to the separation chamber 15 through the annular plate 19 too.

The first part 33 is provided with an inlet valve 39. The inlet valve 39 allows putting the enclosure in communication with the tank 7.

The other port 34, when existing, is provided with an outlet valve similar to the inlet valve 39.

The second port is connected to the pump 5 through a pipe 40 (see FIG. 1).

The low part 37 can also be connected to a pump (not shown in FIGS. 1 and 2)

As shown in FIG. 3a, the inlet valve 39 comprises a chamber 41, an inlet duct 43 and a piston 45. The chamber 41 communicates with the separation chamber 15 through a first aperture 47 in the annular plate 19. The inlet duct communicates with the chamber 41 through a second aperture 49. The inlet duct 45 is adapted to be connected to the tank 7 through a flexible pipe 51 (see FIG. 1) The piston 45 is movable in the chamber 41 between an opening position and a closing position. In the opening position, the piston 45 opens the first 47 and second apertures 49 (FIG. 3a). In the closing position the piston 45 closes the first 47 and second 49 apertures (FIG. 3b). In the opening position, approximately all the space of the chamber 41 comprised between the first 47 and second 49 apertures, forms a free passage.

This passage allows dry chromatography resins to flow from the tank 7 to the separation chamber 15. If a resin comprises particles the size of which is distributed between a minimum size and a maximum size, the minimum section of this passage is calibrated relatively to the maximum size of the particles so as to allow a dry resin to flow through the same without any problem. For example, the minimum section of the passage is at least 10 000 times as large as the particle section of the maximum size particles. This minimum section corresponds to the section of at least one of the first 47 and second 49 apertures. For instance, this minimum section corresponds to a 20 mm internal diameter.

The piston 45 has an end surface 53 with a tapered shape in order both to allow a tight seal with the first aperture 47 and to make the flow through the valve 39 easier. Said end surface 53 is flush with the internal surface of the annular plate 19, when the piston 45 is in its closing position, in order to make the column cleaning easier.

An embodiment example of the loading method according to the invention is described below.

According to this embodiment, a dry resin of a type 60 Silica Gel™ (a trademark of Merck kGaA.) marketed with the reference 107734 by Merck kGaA was loaded into a 180 mm diameter GelTec™ column with a height of 600 mm. This resin has a pore size distribution of 5-20 μm and a mean particle size of 63 to 200 μm. It is contained in a 20 l tank 7.

As shown in FIG. 4, the tank 7 is connected to the first part 33. The sucking of the pump 5 is connected to the second port 35. The vacuum system of the pump 5 goes back to the tank 7. The low part 37 is closed. An inflatable seal that serves as seal between the packing piston and the inner surface of the separation chamber 15 is inflated to 6 bars.

At a depression of −75 kPa in the separation chamber 15, with an inlet valve 39 of 20 mm internal diameter, the flow rate is equal to 500 Kgs of resin per hour, without any problem. The resin bed starts to build itself very constantly. The accumulation of dry resin in front of the inlet valve 39 does not disturb the flow at all. After 2 mn of sucking, the all bed of the 180 mm diameter column is full of dry resin. The pump 5 is then stopped and the resin does settle down very evenly. The packing process can be proceeded.

For columns of larger diameter the two ports 33, 34 can be used, one to suck in the resin and the other one to suck out the air or the two of them to suck in the resin, while the air is sucked out by the second port 35.

An embodiment example of the unloading method according to the invention is described below, with reference to FIG. 5.

The resin is mixed with a liquid through a separation process, and then according to this embodiment, the liquid is first pumped through the low port 37.

The packing piston 25 is raised. The resin is then dried injecting hot air through the low port 37. The hot air naturally rises and carries condensates.

When the resin is dry, air can be injected through the first port 33 in order to make the dried resin cake collapsed.

After that, the dry resin is sucked out through the first port 33 while air is possibly injected through the low port 37 in order to create a small fluidisation above the bottom unpacking piston 31.

After a complete unloading of the resin, the bottom unpacking piston 31 is lowered (dotted line) and the packing piston seal is deflated. The column can be cleaned in a conventional way before being used again.

As a variant, the internal diameter of the inlet valve can be of 30 mm. This allows to rise the flow rate to values of about 600 to 100 Kgs per hour.

The resin can also be unloaded in a conventional way as a resin mixed with a liquid, through the low port 37.

Alternatively, the dry or dampened resin can be unloaded removing the bottom unpacking piston 31 and the bottom base plate 21.

The invention claimed is:

1. A chromatography column comprising:
an enclosure, a first port and a second port,
said first port being provided with an inlet valve,
said enclosure being in communication with a tank via said inlet valve and with a pump via said second port, said tank comprising a dry chromatography resin made of particles having a size distributed between a minimum size and a maximum size,
wherein said inlet valve comprises a chamber, an inlet duct and a piston,
the chamber communicating with the enclosure through a first aperture,
the inlet duct communicating with the chamber through a second aperture and being connected to the tank, and
the piston being movable in the chamber between a closing position, where it closes the first and second apertures, and an opening position, where it opens the first and second apertures and it lets free substantially all the space of the chamber between the first and second apertures.

2. The chromatography column of claim 1, wherein the enclosure, when in use, extends vertically between a bottom and a top, the second port being located above the first port.

3. The chromatography column of claim 1, wherein the valve defines a passage between a pipe connected to the inlet duct and the enclosure, said passage having a minimum section which corresponds to the section of any of the first and second apertures.

4. The chromatography column of claim 3, wherein the minimum section of the passage is at least 10 000 times as large as the particle section corresponding to the maximum size particles.

5. The chromatography column of claim 1, wherein the piston when in closing position has an end surface with a tapered shape, said end surface having a portion which is flush with the internal surface of the enclosure.

6. The chromatography column of claim 1, wherein the first port forms a passage having a minimum section corresponding to at least a minimum internal diameter of 20 mm.

* * * * *